US00PP14077P39

(12) United States Plant Patent
Schmulling

(10) Patent No.: US PP14,077 P3
(45) Date of Patent: Aug. 19, 2003

(54) HELIOTROPE PLANT NAMED 'NAGANO'

(75) Inventor: Markus Schmulling, Billerbeck/Beerlage (DE)

(73) Assignee: Outeniqua Nursery, Emerald (AU)

( * ) Notice: Subject to any disclaimer, the term of this patent is extended or adjusted under 35 U.S.C. 154(b) by 0 days.

(21) Appl. No.: 09/837,581

(22) Filed: Apr. 19, 2001

(65) Prior Publication Data

US 2002/0157147 P1 Oct. 24, 2002

(51) Int. Cl.[7] ..... A01H 5/00
(52) U.S. Cl. ..... Plt./226
(58) Field of Search ..... Plt./226

(56) References Cited

U.S. PATENT DOCUMENTS

PP11,326 P * 4/2000 Schmulling ..... Plt./226

OTHER PUBLICATIONS http://www.greenbeam.com/features/plant032601.stm Thursday's Plant—Plant Picks, Unusual Annuals.* http://www.provenwinners.com/catalog/details.php?ID=457 "nagano PPAF".*

UPOV–ROM GTITM Computer Database, GTI Jouve Retrieval Software 2002/06, citation(s) for 'Nagano'.*

* cited by examiner

*Primary Examiner*—Bruce R. Campell
*Assistant Examiner*—W C Haas
(74) *Attorney, Agent, or Firm*—C. A. Whealy

(57) ABSTRACT

A distinct cultivar of Heliotrope plant named 'Nagano', characterized by its compact and mounded plant habit; freely branching, dense and bushy growth habit; early and freely flowering habit; and dark purple-colored fragrant flowers.

1 Drawing Sheet

BOTANICAL CLASSIFICATION

*Heliotrope arborescens.*

BACKGROUND OF THE INVENTION

The present invention relates to a new and distinct cultivar of Heliotrope plant, botanically known as *Heliotrope arborescens*, and hereinafter referred to by the name 'Nagano'.

The new Heliotrope is a product of a planned breeding program conducted by the Inventor in Billerbeck, Germany. The new Heliotrope originated from a cross made by the Inventor of the Heliotrope cultivar Atlanta, disclosed in U.S. Plant Pat. No. 11,326, as the female, or seed, parent with the Heliotrope cultivar Blue, not patented, as the male, or pollen, parent. The cultivar Nagano was discovered and selected by the Inventor as a flowering plant within the progeny of the stated cross in 1997 in a controlled environment in Temming, Germany. The new Heliotrope was selected on the basis of its dark purple-colored flowers.

Asexual reproduction of the new Heliotrope by cuttings in Temming, Germany, since 1997, has shown that the unique features of this new Heliotrope are stable and reproduced true to type in successive propagations.

SUMMARY OF THE INVENTION

Plants of the new Heliotrope have not been observed under all possible environmental conditions. The phenotype may vary significantly with variations in environment such as temperature and light and fertilizer rates, without, however, any variance in genotype.

The following traits have been repeatedly observed and are determined to be the unique characteristics of plants of the new Heliotrope and differentiate plants of the new Heliotrope from other commercial Heliotrope cultivars:

1. Compact and mounded plant habit.
2. Freely branching, dense and bushy growth habit.
3. Early and freely flowering habit.
4. Dark purple-colored flowers.
5. Fragrant flowers.

Compared to plants ofthe parent cultivars, Atlanta and Blue, plants ofthe new Heliotrope are more compact and have darker colored flowers.

BRIEF DESCRIPTION OF PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new Heliotrope.

The photograph at the top of the sheet comprises a side perspective view of four typical flowering plants of 'Nagano' grown in a 25.5-cm container for 8 weeks.

The photograph at the bottom of the sheet comprises a close-up view of typical flowers and leaves of 'Nagano'.

DETAILED BOTANICAL DESCRIPTION

The following observations, measurements and comparisons describe plants grown in Bonsall, Calif., under commercial practice during the summer and autumn in a polyethylene-covered greenhouse with day temperatures ranging from 18 to 35° C. and night temperatures ranging from 13 to 18° C. Three rooted cuttings were planted in 25.5-cm containers, pinched once and grown for about 8 weeks. In the following description, color references are made to The Royal Horticultural Society Colour Chart except where general terms of ordinary dictionary significance are used.

Botanical classification: *Heliotrope arborescens* cultivar Nagano.

Parentage:

*Female parent.*—*Heliotrope arborescens* cultivar Atlanta, disclosed in U.S. Plant Pat. No. 11,326.

*Male parent.*—*Heliotrope arborescens* cultivar Blue, not patented.

Propagation:

*Type.*—By vegetative cuttings.

*Time to initiate roots, summer.*—About 21 days at 22 to 24° C.

*Time to initiate roots, winter.*—About 24 days at 22 to 24° C.

*Time to produce a rooted cutting, summer or winter.*—About 35 days at 22 to 24° C.

*Root description.*—Fine and fibrous.

*Rooting habit.*—Freely branching.

Plant description:

*Plant form.*—Compact and mounded plant habit. Freely basal branching; typically about 5 lateral branches. Removal of terminal apices enhances development of axillary branching, dense and bushy plant habit.

*Growth habit.*—Lateral shoots upright, then outwardly spreading as plants develop. Moderately vigorous.

*Plant height.*—About 18 cm.

*Plant width.*—About 22.5 cm.

*Stem description.*—Lateral branch length: About 13 cm. Lateral branch diameter: About 4 mm. Internode length: About 1.9 cm. Texture: Very fine pubescence. Color: 143C.

*Foliage description.*—Arrangement/quantity: Single leaves, alternate; about 6 to 10 leaves per lateral branch. Length: About 7 cm. Width: About 2.8 cm. Shape: Elongate, elliptic. Apex: Acute. Base: Acute. Margin: Entire. Texture, both surfaces: Fine pubescence; young leaves, velvety; fully expanded leaves, rough. Venation pattern: Pinnate. Color: Young foliage, upper surface: 147B. Young foliage, lower surface: 144A. Mature foliage, upper surface: 147A; venation, 147B. Mature foliage, lower surface: 147B; venation, 144D. Petiole: Length: About 1.75 mm. Diameter: About 2 mm. Color: 144B.

Flower description:

*Flowering habit.*—Five-parted fused trumpet-shaped flowers arranged in terminal scorpioid cymes; flowers open acropetally. Freely flowering with more than 200 flowers per lateral branch. Flowers are held mostly upright. Flowers persistent.

*Natural flowering season.*—In the garden, spring through autumn; under greenhouse conditions, year-round. Flowers last about 2 to 3 days on the plant.

*Fragrance.*—Sweet, cherry and/or vanilla-like.

*Flower size.*—Cymes are about 6 cm in diameter; individual flowers are about 6 mm in diameter and about 8 mm in height.

*Flower bud.*—Length: About 5 mm. Diameter: About 2.5 mm. Shape: Tubular. Color: 93C.

*Petals.*—Arrangement: Five fused at base, tubular; flaring into a five-lobed trumpet. Length: About 2 mm. Width: About 2 mm. Apex: Rounded. Margin: Entire. Texture: Velvety. Color: When opening, upper surface: 93A. When opening, lower surface: 93B. Opened flower, upper surface; 93C to 93D. Opened flower, lower surface: 93D. Throat: 1A.

*Sepals.*—Quantity/arrangement: Five, fused at base. Shape: Elliptic. Calyx length: About 3 mm. Calyx diameter: About 2 mm. Apex: Acute. Margin: Entire. Texture: Pubescent. Color: Upper surface: 79B. Lower surface: more gray-green than 79A.

*Peduncles.*—Length: About 2 cm. Diameter: About 2.5 mm. Aspect: About 30° from vertical. Strength: Strong. Color: 147B.

*Reproductive organs.*—Stamens: Quantity/arrangement: Five, adnate to base of corolla tube. Anther shape: Elongate, oblong. Anther length: About 1 mm. Anther color: 17B. Pollen amount: Scarce. Pollen color: 17B. Pistils: Quantity: One. Pistil length: About 2 mm. Stigma shape: Rounded. Stigma color: 147C. Style length: About 1 mm. Style color: 147C. Ovary color: 147D.

*Seed production.*—Not observed.

Disease/pest resistance: Plants of the new heliotrope have not been noted to be resistant to known pathogens or pests common to Heliotrope.

I claim:

1. A new and distinct Heliotrope plant named Nagano, as illustrated and described.

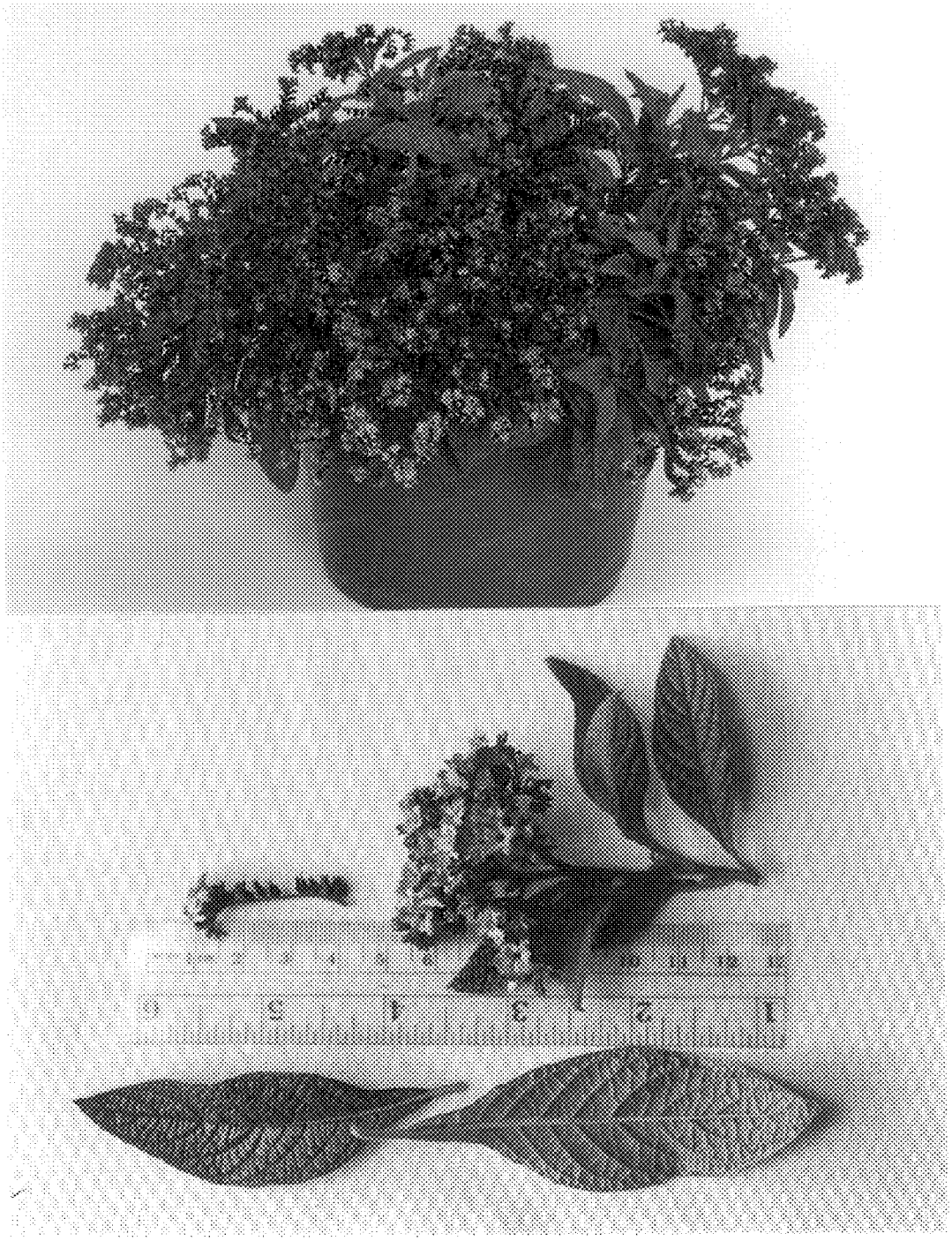

* * * * *